United States Patent
Hirokami et al.

(10) Patent No.: US 9,238,664 B2
(45) Date of Patent: Jan. 19, 2016

(54) SULFUR-CONTAINING ORGANOSILICON COMPOUND, MAKING METHOD, RUBBER COMPOUNDING INGREDIENT, AND RUBBER COMPOSITION

(71) Applicant: Shin-Etsu Chemical Co., Ltd., Tokyo (JP)

(72) Inventors: Munenao Hirokami, Annaka (JP); Kazuhiro Tsuchida, Annaka (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 0 days.

(21) Appl. No.: 14/565,852

(22) Filed: Dec. 10, 2014

(65) Prior Publication Data

US 2015/0166580 A1 Jun. 18, 2015

(30) Foreign Application Priority Data

Dec. 13, 2013 (JP) ................. 2013-257663

(51) Int. Cl.

| | |
|---|---|
| *C07F 7/10* | (2006.01) |
| *C07F 7/18* | (2006.01) |
| *B60C 1/00* | (2006.01) |
| *C08K 5/00* | (2006.01) |
| *C08L 9/06* | (2006.01) |
| *C07F 7/08* | (2006.01) |
| *C08K 5/548* | (2006.01) |

(52) U.S. Cl.
CPC ............ *C07F 7/1836* (2013.01); *B60C 1/00* (2013.01); *C07F 7/1812* (2013.01); *C07F 7/1876* (2013.01); *C08K 5/00* (2013.01); *C08L 9/06* (2013.01); *C07F 7/0818* (2013.01); *C08K 5/548* (2013.01); *C08L 2555/84* (2013.01); *C08L 2555/86* (2013.01)

(58) Field of Classification Search
CPC ..... C08K 5/548; C07F 7/1836; C07F 7/1812; C07F 7/0818; C08L 2555/84; C08L 2555/86
USPC ....................................................... 556/427
See application file for complete search history.

(56) References Cited

U.S. PATENT DOCUMENTS

| | | |
|---|---|---|
| 6,229,036 B1 | 5/2001 | Batz-Sohn et al. |
| 6,414,061 B1 | 7/2002 | Cruse et al. |
| 6,777,569 B1 | 8/2004 | Westmeyer et al. |
| 7,199,256 B2 | 4/2007 | Yanagisawa et al. |
| 7,217,751 B2 | 5/2007 | Durel et al. |
| 7,423,165 B2 | 9/2008 | Korth et al. |
| 8,093,323 B2 | 1/2012 | Saiki et al. |
| 8,097,743 B2 | 1/2012 | Glatzer et al. |
| 2013/0317151 A1* | 11/2013 | Yagi ..................... B60C 1/00 524/224 |

FOREIGN PATENT DOCUMENTS

| | | |
|---|---|---|
| CN | 103450504 A | 12/2013 |
| EP | 2 644 650 | * 10/2013 |
| EP | 2 644 650 A1 | 10/2013 |
| JP | 51-20208 | 6/1976 |
| JP | 2002-145890 A | 5/2002 |
| JP | 2004-18511 A | 1/2004 |
| JP | 2004-525230 A | 8/2004 |
| JP | 2005-8639 A | 1/2005 |
| JP | 2008-150546 A | 7/2008 |
| JP | 2008-169157 A | 7/2008 |
| JP | 2010-132604 A | 6/2010 |
| JP | 4571125 B2 | 10/2010 |
| WO | WO 2009/104766 A1 | 8/2009 |
| WO | WO 2012/070625 A1 | 5/2012 |

OTHER PUBLICATIONS

Extended European Search Report issued Apr. 15, 2015, in European Patent Application No. 14196635.8.
U.S. Appl. No. 60/423,577, filed Nov. 4, 2002.

* cited by examiner

*Primary Examiner* — Margaret Moore
(74) *Attorney, Agent, or Firm* — Birch, Stewart, Kolasch & Birch, LLP

(57) ABSTRACT

A sulfur-containing organosilicon compound having a hydrolyzable silyl group, sulfide group and amide group is shelf stable and useful as a rubber compounding ingredient. When compounded in a rubber composition, the organosilicon compound is effective for significantly reducing the hysteresis loss and improving the abrasion resistance of the rubber composition.

11 Claims, No Drawings

SULFUR-CONTAINING ORGANOSILICON COMPOUND, MAKING METHOD, RUBBER COMPOUNDING INGREDIENT, AND RUBBER COMPOSITION

CROSS-REFERENCE TO RELATED APPLICATION

This non-provisional application claims priority under 35 U.S.C. §119(a) on Patent Application No. 2013-257663 filed in Japan on Dec. 13, 2013, the entire contents of which are hereby incorporated by reference.

TECHNICAL FIELD

This invention relates to a sulfur-containing organosilicon compound having a hydrolyzable silyl group, sulfide group and amide group in its molecule, a method for preparing the same, a rubber compounding ingredient comprising the same, a rubber composition having the rubber compounding ingredient compounded therein, and a tire comprising the rubber composition.

BACKGROUND ART

Sulfur-containing organosilicon compounds are useful as an essential component of silica-filled rubber compositions for the manufacture of tires. Silica-filled tires have improved performance in the automotive application, especially abrasion resistance, low rolling resistance and wet grip. Such tire performance improvements are closely related to fuel consumption savings, with great efforts being currently devoted to this end.

For fuel consumption savings, it is essential to increase the silica filling factor of rubber compositions. While silica-filled rubber compositions are effective for providing tires with reduced rolling resistance and improved wet grip, they suffer from working problems including a high green viscosity and necessary multi-stage milling. When inorganic fillers such as silica are merely compounded in rubber, the resulting rubber compositions are substantially low in breaking strength and abrasion resistance on account of short filler dispersion. Then sulfur-containing organosilicon compounds are essential for improving the dispersion of inorganic filler in rubber and chemically bonding the filler to the rubber matrix.

Of the sulfur-containing organosilicon compounds, those compounds having alkoxysilyl and polysulfide groups in the molecule, for example, bis(triethoxysilylpropyl)tetrasulfide and bis(triethoxysilylpropyl)disulfide are known effective.

Besides the above organosilicon compounds having a polysulfide group, a product obtained from transesterification reaction of a sulfide-containing organosilicon compound with an alkyl alcohol amine is known to contribute to substantial improvements in fuel consumption and abrasion resistance as disclosed in Patent Documents 12 and 13. The sulfur-containing organosilicon compounds described in these patent documents, however, are poor in shelf stability and awkward to handle.

CITATION LIST

Patent Document 1: JP-B S51-20208
Patent Document 2: JP-A 2004-525230
Patent Document 3: JP-A 2004-018511
Patent Document 4: JP-A 2005-008639
Patent Document 5: JP-A 2002-145890
Patent Document 6: JP-A 2008-150546
Patent Document 7: JP-A 2010-132604
Patent Document 8: JP 4571125
Patent Document 9: U.S. Provisional Patent Application 60/423,577
Patent Document 10: U.S. Pat. No. 6,229,036
Patent Document 11: U.S. Pat. No. 6,414,061
Patent Document 12: JP-A 2008-169157 (U.S. Pat. No. 8,093,323)
Patent Document 13: WO 2009/104766

DISCLOSURE OF INVENTION

An object of the invention is to provide a sulfur-containing organosilicon compound which is shelf stable and ensures that a rubber composition comprising the organosilicon compound has a low hysteresis loss and improved abrasion resistance, a method for preparing the same, a rubber compounding ingredient comprising the same, and a rubber composition.

The inventors have found that a rubber composition in which a rubber compounding ingredient comprising a sulfur-containing organosilicon compound having a hydrolyzable silyl group, sulfide group and amide group in its molecule is compounded meets the desired low fuel consumption tire characteristics.

In a first aspect, the invention provides a sulfur-containing organosilicon compound obtained from transesterification reaction of a sulfide-containing organosilicon compound with an amide compound. The sulfide-containing organosilicon compound has the formula (1):

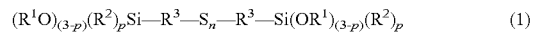

$$(R^1O)_{(3-p)}(R^2)_p Si-R^3-S_n-R^3-Si(OR^1)_{(3-p)}(R^2)_p \quad (1)$$

wherein $R^1$ and $R^2$ are each independently a monovalent hydrocarbon group of 1 to 4 carbon atoms, $R^3$ is a divalent hydrocarbon group of 1 to 10 carbon atoms, n is a number having an average value in the range of 2≤n≤6, and p is an integer of 0 to 2, and the amide compound has the formula (2):

(2)

wherein $R^4$ is a monovalent hydrocarbon group of 1 to 20 carbon atoms, $R^5$ is a group of the formula (3), and $R^6$ is hydrogen, an alkyl group of 1 to 12 carbon atoms, an aryl group of 6 to 12 carbon atoms or a group of the formula (3):

$$*-(CH_2)_s-R^7-OH \quad (3)$$

wherein $R^7$ is an alkylene group of 1 to 12 carbon atoms or $*-O-(Y-O)_m-Y-*$, Y is an alkylene group of 1 to 10 carbon atoms, m is a number of 1 to 40, and s is a number of 0 to 12, and *designates a bonding site.

In a preferred embodiment, the amide compound having formula (2) is selected from compounds having the formulae (4) to (7):

(4)

$$R^4-\underset{\underset{O}{\|}}{C}-\underset{\underset{R^6}{|}}{N}-(CH_2)_s-OH \quad (5)$$

$$R^4-\underset{\underset{O}{\|}}{C}-\underset{\underset{R^6}{|}}{N}-C_2H_4-(O-C_2H_4-O)_q-H \quad (6)$$

$$R^4-\underset{\underset{O}{\|}}{C}-\underset{\underset{R^6}{|}}{N}-C_3H_6-(O-C_3H_6-O)_q-H \quad (7)$$

wherein $R^4$, $R^6$ and s are as defined above, and q is a number of 1 to 40.

In a preferred embodiment, during the reaction, 1 to 200 parts by weight of the amide compound having formula (2) is used per 100 parts by weight of the sulfide-containing organosilicon compound having formula (1).

In a second aspect, the invention provides a method for preparing a sulfur-containing organosilicon compound comprising transesterification reaction of a sulfide-containing organosilicon compound having the formula (1), defined above, with an amide compound having the formula (2), defined above, in the presence of a catalyst.

Preferably the amide compound having formula (2) is selected from compounds having the formulae (4) to (7), defined above.

In a preferred embodiment, 1 to 200 parts by weight of the amide compound having formula (2) is used per 100 parts by weight of the sulfide-containing organosilicon compound having formula (1).

The catalyst is typically an acid, alkaline metal alcoholate, or organometallic catalyst.

In a third aspect, the invention provides a rubber compounding ingredient comprising the sulfur-containing organosilicon compound defined above.

The rubber compounding ingredient may further comprise at least one powder. In this embodiment, the sulfur-containing organosilicon compound (A) and the powder (B) are present in a weight ratio A/B of 70/30 to 5/95.

Also contemplated herein are a rubber composition comprising the rubber compounding ingredient defined above, and a tire comprising the rubber composition.

Advantageous Effects of Invention

The sulfur-containing organosilicon compound having a hydrolyzable silyl group, sulfide group and amide group is effective for substantially reducing the hysteresis loss of a silica-filled rubber composition because the interaction of amide group with silica in the rubber composition enhances reactivity and dispersibility in proximity to silica. The rubber composition meets the desired low fuel consumption tire characteristics. The organosilicon compound is shelf stable by virtue of the starting amide compound.

DESCRIPTION OF PREFERRED EMBODIMENTS

As used herein, the term "silane coupling agent" is encompassed in the term "organosilicon compound".
Sulfur-Containing Organosilicon Compound (Silane Coupling Agent)

The sulfur-containing organosilicon compound is obtained from transesterification reaction of a sulfide-containing organosilicon compound with an amide compound in the presence of a catalyst. The sulfide-containing organosilicon compound has the formula (1):

$$(R^1O)_{(3-p)}(R^2)_pSi-R^3-S_n-R^3-Si(OR^1)_{(3-p)}(R^2)_p \quad (1)$$

wherein $R^1$ and $R^2$ are each independently a monovalent hydrocarbon group of 1 to 4 carbon atoms, $R^3$ is a divalent hydrocarbon group of 1 to 10 carbon atoms, n is a number having an average value in the range of $2 \leq n \leq 6$, and p is an integer of 0 to 2. The amide compound has the formula (2):

$$R^4-\underset{\underset{O}{\|}}{C}-\underset{\underset{R^5}{|}}{N}-R^6 \quad (2)$$

wherein $R^4$ is a monovalent hydrocarbon group of 1 to 20 carbon atoms, $R^5$ is a group of the formula (3), and $R^6$ is hydrogen, an alkyl group of 1 to 12 carbon atoms, an aryl group of 6 to 12 carbon atoms or a group of the formula (3):

$$*-(CH_2)_s-R^7-OH \quad (3)$$

wherein $R^7$ is an alkylene group of 1 to 12 carbon atoms or $*-O-(Y-O)_m-Y-*$, Y is an alkylene group of 1 to 10 carbon atoms, m is a number of 1 to 40, and s is a number of 0 to 12, and * designates a bonding site.

In formula (1), $R^1$ and $R^2$ each are a monovalent hydrocarbon group of 1 to 4 carbon atoms, examples of which include alkyl and alkenyl groups such as methyl, ethyl, n-propyl, i-propyl, n-butyl, i-butyl, t-butyl, vinyl, allyl, and methallyl. $R^3$ is a divalent hydrocarbon group of 1 to 10 carbon atoms, examples of which include alkylene, arylene and alkenylene groups such as methylene, ethylene, propylene, n-butylene, i-butylene, hexylene, decylene, phenylene, and methylphenylethylene, and combinations thereof. The subscript n is a number having an average value in the range of $2 \leq n \leq 6$, preferably $2 \leq n \leq 4$, and p is 0, 1 or 2, preferably 0 or 1, and most preferably 0.

Typical examples of the compound having formula (1) are given below, but not limited thereto.

$(CH_3O)_3Si-(CH_2)_3-S_4-(CH_2)_3-Si(OCH_3)_3$ $(CH_3O)_3Si-(CH_2)_3-S_3-(CH_2)_3-Si(OCH_3)_3$ $(CH_3O)_3Si-(CH_2)_3-S_2-(CH_2)_3-Si(OCH_3)_3$ $(CH_3CH_2O)_3Si-(CH_2)_3-S_4-(CH_2)_3-Si(OCH_2CH_3)_3$ $(CH_3CH_2O)_3Si-(CH_2)_3-S_3-(CH_2)_3-Si(OCH_2CH_3)_3$ $(CH_3CH_2O)_3Si-(CH_2)_3-S_2-(CH_2)_3-Si(OCH_2CH_3)_3$

In formula (2), $R^4$ is a monovalent hydrocarbon group of 1 to 20 carbon atoms, examples of which include alkyl groups such as methyl, ethyl, propyl, butyl, hexyl, octyl, decyl, dodecyl, tetradecyl, hexadecyl and octadecyl, and alkenyl groups such as vinyl, allyl, hexenyl, octenyl, decenyl, dodecenyl, tetradecenyl, hexadecenyl, and octadecenyl.

$R^5$ is a group of the formula (3).

$$*-(CH_2)_s-R^7-OH \quad (3)$$

Herein $R^7$ is an alkylene group of 1 to 12 carbon atoms or $*-O-(Y-O)_m-Y-*$, Y is an alkylene group of 1 to 10 carbon atoms, m is a number of 1 to 40, and s is a number of 0 to 12, and * designates a bonding site (the same hereinafter).

Examples of the alkylene group of 1 to 12 carbon atoms include methylene, ethylene, propylene, butylene, hexylene, octylene, decylene, and dodecylene. Examples of the alkylene group of 1 to 10 carbon atoms include methylene, ethylene, propylene, butylene, hexylene, octylene, and decylene.

$R^6$ is hydrogen, an alkyl group of 1 to 12 carbon atoms, an aryl group of 6 to 12 carbon atoms or a group of the formula (3). Examples of the alkyl group of 1 to 12 carbon atoms include methyl, ethyl, propyl, butyl, hexyl, octyl, decyl, and dodecyl. Examples of the aryl group of 6 to 12 carbon atoms include phenyl, naphthyl, tolyl, xylyl, and ethylphenyl. Examples of the group having formula (3) include, but are not limited to, *—$CH_2$—OH, *—$C_2H_4$—OH, *—$C_3H_6$—OH, *—$C_2H_4$—O—$C_2H_4$—OH, *—$(C_2H_4O)_2$—$C_2H_4$—OH, *—$(C_2H_4O)_3$—$C_2H_4$—OH, *—$(C_2H_4O)_4$—$C_2H_4$—OH, *—$(C_2H_4O)_5$—$C_2H_4$—OH, *—$(C_3H_6O)_2$—$C_3H_6$—OH, *—$(C_3H_6O)_3$—$C_3H_6$—OH, *—$(C_3H_6O)_4$—$C_3H_6$—OH, and *—$(C_3H_6O)_5$—$C_3H_6$—OH.

Preferred examples of the amide compound having formula (2) are those compounds of the following formulae (4) to (7).

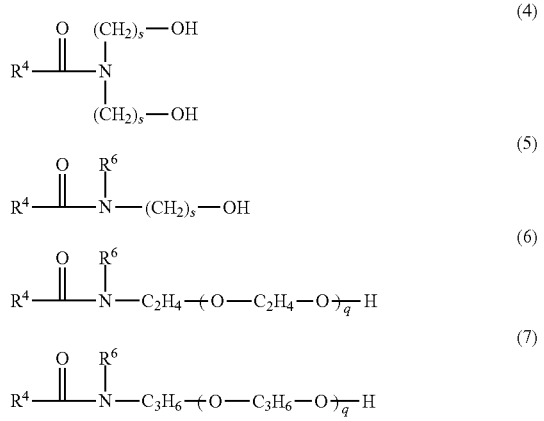

Herein $R^4$, $R^6$ and s are as defined above, and q is a number of 1 to 40.

The compounds of formula (4) are commercially available as Amisol CDE, Amisol LDE, Amisol FDE, Amisol KD-1, Aminone L-02, and Aminone PK-02. The compounds of formula (5) are commercially available as Amisol CME, Amisol LME, Amisol PLME-A, and Aminone C-11S. The compounds of formula (6) are commercially available as Amizett 2C, Amizett 5C, Amizett 10C, Amizett 2L and Amizett 5L. The compound of formula (7) is commercially available as Amizett 1PC. Notably trade-marks Amisol and Amizett are of Kawaken Fine Chemical Co., Ltd., and Aminone is of Kao Corp.

In the reaction, 1 to 200 parts by weight of the amide compound having formula (2) is preferably used per 100 parts by weight of the sulfide-containing organosilicon compound having formula (1). The amount of the amide compound having formula (2) is more preferably 2 to 100 parts by weight, and even more preferably 10 to 80 parts by weight.

The catalyst used to promote transesterification reaction between the organosilicon compound having formula (1) and the amide compound having formula (2) is preferably selected from acid, alkaline metal alcoholate, and organometallic catalysts. Suitable acid catalysts include organic acids such as trifluoromethanesulfonic acid, p-toluenesulfonic acid, pyridinium p-toluenesulfonate, and camphorsulfonic acid, and mineral acids such as hydrochloric acid, sulfuric acid and phosphoric acid. Suitable alkaline metal alcoholate catalysts include sodium methoxide, sodium ethoxide, potassium ethoxide, potassium methoxide, and lithium ethoxide. Suitable organometallic catalysts include titanium-based compounds such as tetramethoxytitanium, tetraethoxytitanium, tetrabutoxytitanium, and tetrapropoxytitanium, and tin-based compounds such as dibutyltin oxide, methylphenyltin oxide, tetraethyltin, and hexaethyltin oxide.

Although the amount of the catalyst used is not particularly limited, it is preferably 0.0001 to 10% by weight, more preferably 0.0001 to 1% by weight based on the sulfide-containing organosilicon compound having formula (1).

Since the sulfur-containing organosilicon compound is the transesterification reaction product of a sulfide-containing organosilicon compound having formula (1) with an amide-containing alcohol having formula (2), the sulfur-containing organosilicon compound resulting from reaction differs depending on the functionality of the alcohol used. The sulfur-containing organosilicon compound may be a mixture of two or more organosilicon compounds as shown below, but not limited thereto.

Referring to the reaction of an organosilicon compound having trialkoxysilyl groups with a monohydric alcohol as a first example, there may be produced an unreacted sulfide-containing organosilicon compound, a reaction product having one alkoxysilyl group transesterified, a reaction product having two alkoxysilyl groups transesterified, a reaction product having three alkoxysilyl groups transesterified, a reaction product having four alkoxysilyl groups transesterified, a reaction product having five alkoxysilyl groups transesterified, and a reaction product having six alkoxysilyl groups transesterified. The reaction products are not limited to the organosilicon compounds shown below.

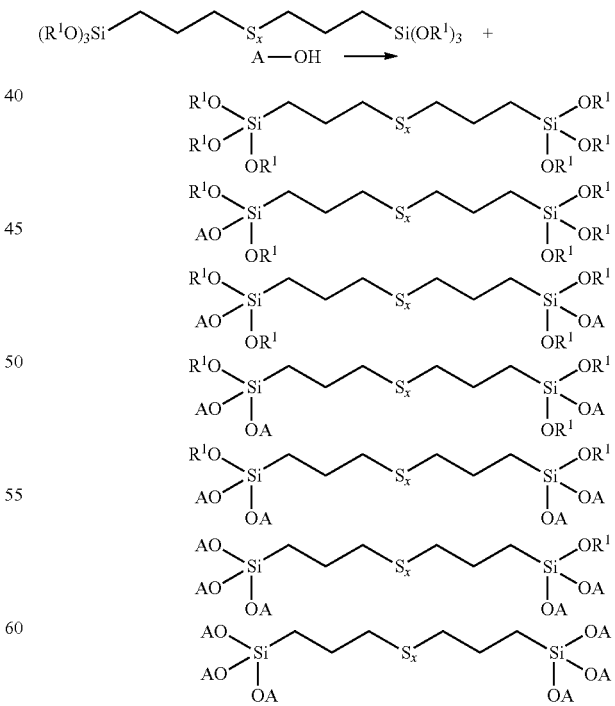

Herein $R^1$ is as defined above, A is the residue of an amide compound of formula (2) having one OH group, and x is a number having an average value in the range of $2 \leq x \leq 6$.

Referring to the reaction of an organosilicon compound having trialkoxysilyl groups with a dihydric alcohol as a second example, there may be produced an unreacted sulfide-containing organosilicon compound, a reaction product having two alcohol moieties transesterified in the molecule, a reaction product having two alcohol moieties transesterified between two molecules, a reaction product crosslinked with dialcohol links over multiple molecules, a reaction product of sulfide-containing organosilicon compound having two alcohol moieties transesterified in one molecule and crosslinked with a dialcohol link, and a reaction product of sulfide-containing organosilicon compound having two alcohol moieties transesterified in one molecule and crosslinked with dialcohol links over multiple molecules. The reaction products are not limited to the organosilicon compounds shown below.

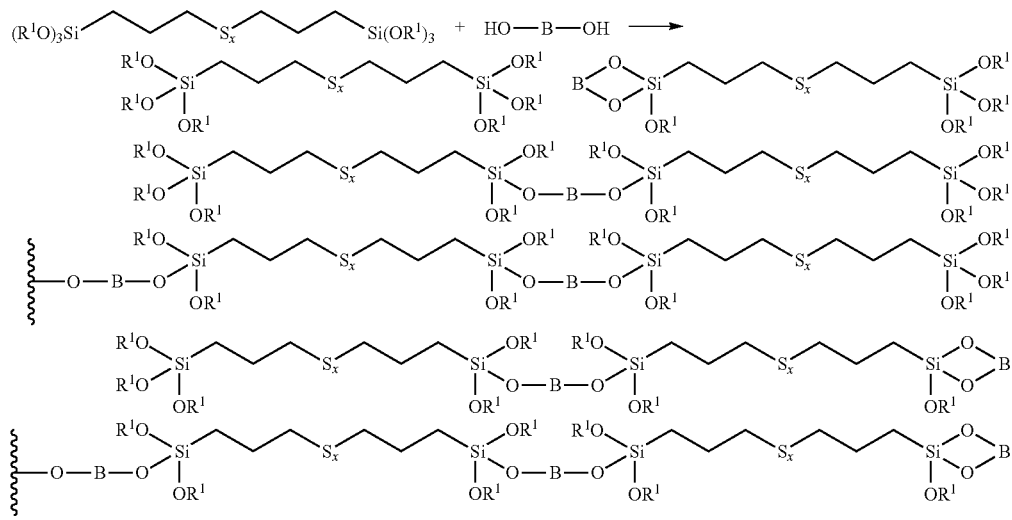

Herein $R^1$ is as defined above, B is the residue of an amide compound of formula (2) having two OH groups, and x is a number having an average value in the range of $2 \leq x \leq 6$.

Preparation of Sulfur-Containing Organosilicon Compound (Silane Coupling Agent)

The second embodiment of the invention is a method for preparing a sulfur-containing organosilicon compound comprising transesterification reaction of a sulfide-containing organosilicon compound with an amide compound in the presence of a catalyst, the sulfide-containing organosilicon compound having the formula (1):

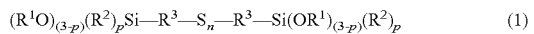

wherein $R^1$, $R^2$, $R^3$, n, and p are as defined above, and the amide compound having the formula (2):

wherein $R^4$, $R^5$, and $R^6$ are as defined above. If desired, a solvent may be used in the preparation of the organosilicon compound. The solvent used herein is not particularly limited as long as it is inert to the reactants, sulfide-containing organosilicon compound and amide compound. Suitable solvents include aliphatic hydrocarbon solvents such as pentane, hexane, heptane, and decane, aromatic hydrocarbon solvents such as benzene, toluene, and xylene, and ether solvents such as diethyl ether, tetrahydrofuran, and 1,4-dioxane.

During the preparation of the organosilicon compound, the reaction temperature is not particularly limited as long as effective reaction runs. Preferably the reaction temperature is 20 to 150° C., more preferably 60 to 120° C. The reaction time is not particularly limited as long as the reaction is completed. Preferably the reaction time is 10 minutes to 24 hours, more preferably 1 to 15 hours.

Rubber Compounding Ingredient

The third embodiment is a rubber compounding ingredient comprising (A) the sulfur-containing organosilicon compound defined herein and optionally, (B) at least one powder. Examples of the powder (B) include carbon black, talc, calcium carbonate, stearic acid, silica, aluminum hydroxide, alumina, and magnesium hydroxide. Of these, silica and aluminum hydroxide are preferred for reinforcement, with silica being most preferred.

Preferably, the organosilicon compound (A) and the powder (B) are combined in a weight ratio A/B of 70/30 to 5/95, more preferably 60/40 to 10/90. Outside the range, a rubber compounding ingredient containing a less amount of powder (B) may become liquid and difficult to charge a rubber mill therewith. If the amount of powder (B) is excessive, which means that powder (B) accounts for the majority of the rubber compounding ingredient, the transportation cost of rubber compounding ingredient may be increased.

Additional components may be added to the rubber compounding ingredient. Suitable additional components include fatty acids, fatty acid salts, organic polymers and rubbers such as polyethylene, polypropylene, polyoxyalkylene, polyester, polyurethane, polystyrene, polybutadiene, polyisoprene, natural rubber, and styrene-butadiene copolymer, as well as additives commonly used in tires and general rubber compositions such as vulcanizers, crosslinkers, vulcanization accelerators, crosslinking accelerators, oils, antioxidants, fillers and plasticizers. These additional components may be either liquid or solid, and may also be diluted with organic solvents or emulsified prior to addition.

Rubber Composition

The rubber compounding ingredient of the invention finds use in silica-filled rubber compositions. The rubber compounding ingredient is preferably added to the filler-loaded rubber composition in such amounts that 0.2 to 30 parts, more preferably 1 to 20 parts by weight of the organosilicon compound is available per 100 parts by weight of the filler. Outside the range, a less amount of the organosilicon compound may fail to obtain the desired rubber physical properties whereas an excessive amount of the organosilicon compound is uneconomical because its effect may be saturated.

The rubber composition in which the rubber compounding ingredient is compounded is based on a rubber, which may be any of rubbers commonly used in prior art rubber compositions. Suitable rubbers include natural rubber (NR), isoprene rubber (IR), various diene rubbers such as styrene-butadiene copolymer rubbers (SBR), polybutadiene rubbers (BR), acrylonitrile-butadiene copolymer rubbers (NBR), and butyl rubber (IIR), and ethylene-propylene copolymer rubbers (EPR, EPDM), which may be used alone or in any blend. Examples of the filler include silica, talc, clay, aluminum hydroxide, magnesium hydroxide, calcium carbonate, and titanium oxide.

Customary additives may be added to the rubber composition in which the rubber compounding ingredient is compounded. Suitable additives are those commonly used in tires and general rubber compositions, such as carbon black, vulcanizers, crosslinkers, vulcanization accelerators, crosslinking accelerators, oils, antioxidants, fillers and plasticizers. The amounts of these additives may be as usual as long as the objects of the invention are not impaired.

In the rubber composition, the organosilicon compound of the invention may serve as a replacement to well-known silane coupling agents. It is thus optional to add another silane coupling agent. There may be added any of silane coupling agents which are used along with silica filler in the prior art. Typical examples include vinyltrimethoxysilane, vinyltriethoxysilane, γ-glycidoxypropyltrimethoxysilane, γ-glycidoxypropyltriethoxysilane, γ-aminopropyltriethoxysilane, β-aminoethyl-γ-aminopropyltrimethoxysilane, β-aminoethyl-γ-aminopropyltriethoxysilane, γ-mercaptopropyltrimethoxysilane, γ-mercaptopropyltriethoxysilane, γ-methacryloxypropyltrimethoxysilane, γ-methacryloxypropyltriethoxysilane, γ-acryloxypropyltrimethoxysilane, γ-acryloxypropyltriethoxysilane, bis(triethoxysilylpropyl)tetrasulfide, and bis(triethoxysilylpropyl) disulfide.

The rubber composition in which the rubber compounding ingredient is incorporated may be prepared and used by any standard procedure including mixing (or kneading) and vulcanization (or crosslinking).

The invention further provides a tire comprising the rubber composition, specifically a tire including a tread made of the rubber composition. The tire is characterized by a significant reduction of rolling resistance and a significant improvement in abrasion resistance. The tire of the invention may have any well-known structures and be manufactured by any standard methods. In an embodiment wherein the tire is a pneumatic tire, the gas with which the tire is filled may be any of normal air, air having a controlled oxygen partial pressure, and inert gases such as nitrogen, argon and helium.

EXAMPLE

Examples of the invention are given below by way of illustration and not by way of limitation. In Examples, the viscosity is measured at 25° C. by a capillary kinematic viscometer. All parts are by weight.

Example 1

A 2-L separable flask equipped with a stirrer, reflux condenser, dropping funnel and thermometer was charged with 539.0 g (1.0 mol) of bis(triethoxysilylpropyl)tetrasulfide (KBE-846 by Shin-Etsu Chemical Co., Ltd.), 143.7 g of lauric acid diethanolamide (Aminone L-02 by Kao Corp.), and 500 g of xylene and heated at 120° C. in an oil bath. Then 0.03 g of tetrabutoxytitanium was admitted to the contents, which were heated and stirred at 120° C. for 5 hours. Subsequent vacuum concentration on a rotary evaporator yielded 623.5 g of the reaction product, which was a brown clear liquid having a viscosity of 83 mm$^2$/s. The sulfur-containing organosilicon compound thus obtained is designated Organosilicon Compound #1.

Example 2

A 2-L separable flask equipped with a stirrer, reflux condenser, dropping funnel and thermometer was charged with 539.0 g (1.0 mol) of bis(triethoxysilylpropyl)tetrasulfide (KBE-846 by Shin-Etsu Chemical Co., Ltd.), 143.7 g of lauric acid diethanolamide (Aminone L-02 by Kao Corp.), and 500 g of xylene and heated at 120° C. in an oil bath. Then 0.6 g of trifluoromethanesulfonic acid was admitted to the contents, which were heated and stirred at 120° C. for 10 hours. Thereafter, 6.0 g of hydrotalcite (Kyoward 500 by Kyowa Chemical Industry Co., Ltd.) was added, followed by stirring at room temperature for 2 hours. Subsequent vacuum concentration on a rotary evaporator and filtration yielded 618.9 g of the reaction product, which was a brown clear liquid having a viscosity of 100 mm$^2$/s. The sulfur-containing organosilicon compound thus obtained is designated Organosilicon Compound #2.

Example 3

A 2-L separable flask equipped with a stirrer, reflux condenser, dropping funnel and thermometer was charged with 539.0 g (1.0 mol) of bis(triethoxysilylpropyl)tetrasulfide (KBE-846 by Shin-Etsu Chemical Co., Ltd.), 128.7 g of coconut oil fatty acid N-methylethanolamide (Aminone C-11S by Kao Corp.), and 500 g of xylene and heated at 120° C. in an oil bath. Then 0.03 g of tetrabutoxytitanium was admitted to the contents, which were heated and stirred at 120° C. for 5 hours. Subsequent vacuum concentration on a rotary evaporator yielded 623.5 g of the reaction product, which was a brown clear liquid having a viscosity of 153 mm$^2$/s. The sulfur-containing organosilicon compound thus obtained is designated Organosilicon Compound #3.

Example 4

A 2-L separable flask equipped with a stirrer, reflux condenser, dropping funnel and thermometer was charged with 539.0 g (1.0 mol) of bis(triethoxysilylpropyl)tetrasulfide (KBE-846 by Shin-Etsu Chemical Co., Ltd.), 128.7 g of coconut oil fatty acid N-methylethanolamide (Aminone C-11S by Kao Corp.), and 500 g of xylene and heated at 120° C. in an oil bath. Then 0.6 g of trifluoromethanesulfonic acid was admitted to the contents, which were heated and stirred at 120° C. for 10 hours. Thereafter, 6.0 g of hydrotalcite (Kyoward 500 by Kyowa Chemical Industry Co., Ltd.) was added, followed by stirring at room temperature for 2 hours. Subsequent vacuum concentration on a rotary evaporator and filtration yielded 620.9 g of the reaction product, which was a brown clear liquid having a viscosity of 160 mm$^2$/s. The sulfur-containing organosilicon compound thus obtained is designated Organosilicon Compound #4.

Example 5

A 2-L separable flask equipped with a stirrer, reflux condenser, dropping funnel and thermometer was charged with 539.0 g (1.0 mol) of bis(triethoxysilylpropyl)tetrasulfide (KBE-846 by Shin-Etsu Chemical Co., Ltd.), 121.7 g of coconut oil fatty acid monoethanolamide (Amizole CME by Kawaken Fine Chemical Co., Ltd.), and 500 g of xylene and heated at 120° C. in an oil bath. Then 0.6 g of trifluoromethanesulfonic acid was admitted to the contents, which were heated and stirred at 120° C. for 10 hours. Thereafter, 6.0 g of hydrotalcite (Kyoward 500 by Kyowa Chemical Industry Co., Ltd.) was added, followed by stirring at room temperature for 2 hours.

Subsequent vacuum concentration on a rotary evaporator and filtration yielded 617.2 g of the reaction product, which was a brown clear liquid having a viscosity of 160 mm$^2$/s. The sulfur-containing organosilicon compound thus obtained is designated Organosilicon Compound #5.

Example 6

A 2-L separable flask equipped with a stirrer, reflux condenser, dropping funnel and thermometer was charged with 539.0 g (1.0 mol) of bis(triethoxysilylpropyl)tetrasulfide (KBE-846 by Shin-Etsu Chemical Co., Ltd.), 143.7 g of polyoxyethylene(2) coconut oil fatty acid monoethanolamide (Amizett 2C by Kawaken Fine Chemical Co., Ltd.), and 500 g of xylene and heated at 120° C. in an oil bath. Then 0.6 g of trifluoromethanesulfonic acid was admitted to the contents, which were heated and stirred at 120° C. for 10 hours. Thereafter, 6.0 g of hydrotalcite (Kyoward 500 by Kyowa Chemical Industry Co., Ltd.) was added, followed by stirring at room temperature for 2 hours. Subsequent vacuum concentration on a rotary evaporator and filtration yielded 638.1 g of the reaction product, which was a brown clear liquid having a viscosity of 69 mm$^2$/s. The sulfur-containing organosilicon compound thus obtained is designated Organosilicon Compound #6.

Example 7

A 2-L separable flask equipped with a stirrer, reflux condenser, dropping funnel and thermometer was charged with 539.0 g (1.0 mol) of bis(triethoxysilylpropyl)tetrasulfide (KBE-846 by Shin-Etsu Chemical Co., Ltd.), 209.8 g of polyoxyethylene(5) coconut oil fatty acid monoethanolamide (Amizett 5C by Kawaken Fine Chemical Co., Ltd.), and 500 g of xylene and heated at 120° C. in an oil bath. Then 0.6 g of trifluoromethanesulfonic acid was admitted to the contents, which were heated and stirred at 120° C. for 10 hours. Thereafter, 6.0 g of hydrotalcite (Kyoward 500 by Kyowa Chemical Industry Co., Ltd.) was added, followed by stirring at room temperature for 2 hours. Subsequent vacuum concentration on a rotary evaporator and filtration yielded 700.3 g of the reaction product, which was a brown clear liquid having a viscosity of 302 mm$^2$/s. The sulfur-containing organosilicon compound thus obtained is designated Organosilicon Compound #7.

Comparative Example 1

A 2-L separable flask equipped with a stirrer, reflux condenser, dropping funnel and thermometer was charged with 539.0 g (1.0 mol) of bis(triethoxysilylpropyl)tetrasulfide (KBE-846 by Shin-Etsu Chemical Co., Ltd.), 59.6 g (0.5 mol) of N-methyldiethanolamine, and 500 g of xylene and heated at 120° C. in an oil bath. Then 0.03 g of tetrabutoxytitanium was admitted to the contents, which were heated and stirred at 120° C. for 5 hours. Subsequent vacuum concentration on a rotary evaporator yielded 545.1 g of the reaction product, which was a brown clear liquid having a viscosity of 42 mm$^2$/s. The sulfur-containing organosilicon compound thus obtained is designated Organosilicon Compound #8.

Comparative Example 2

A 2-L separable flask equipped with a stirrer, reflux condenser, dropping funnel and thermometer was charged with 539.0 g (1.0 mol) of bis(triethoxysilylpropyl)tetrasulfide (KBE-846 by Shin-Etsu Chemical Co., Ltd.), 74.6 g (0.5 mol) of triethanolamine, and 500 g of xylene and heated at 120° C. in an oil bath. Then 0.03 g of tetrabutoxytitanium was admitted to the contents, which were heated and stirred at 120° C. for 5 hours. Subsequent vacuum concentration on a rotary evaporator yielded 538.5 g of the reaction product, which was a brown clear liquid having a viscosity of 122 mm$^2$/s. The sulfur-containing organosilicon compound thus obtained is designated Organosilicon Compound #9.

Examples 8 to 14 and Comparative Examples 3 and 4

The sulfur-containing organosilicon compounds synthesized in Examples 1 to 7 and Comparative Examples 1 and 2 were examined for shelf stability by the following test. The results are shown in Table 1.

A 50-ml glass vial was charged with 20 g of the organosilicon compound. The open vial was held in a thermostatic chamber of 40° C. and RH 50% while the state of the sample was examined after 1 week, 2 weeks and 1 month.

| Rating | Remarks |
| --- | --- |
| ○ | intact (kept liquid) |
| Δ | partially solidified |
| X | completely solidified (gelled) |

TABLE 1

| | Sulfur-containing organosilicon compound | After 1 week | After 2 weeks | After 1 month |
| --- | --- | --- | --- | --- |
| Example 8 | Organosilicon Compound #1 | ○ | Δ | X |
| Example 9 | Organosilicon Compound #2 | ○ | ○ | Δ |
| Example 10 | Organosilicon Compound #3 | ○ | Δ | X |
| Example 11 | Organosilicon Compound #4 | ○ | ○ | Δ |
| Example 12 | Organosilicon Compound #5 | ○ | ○ | Δ |
| Example 13 | Organosilicon Compound #6 | ○ | ○ | Δ |
| Example 14 | Organosilicon Compound #7 | ○ | ○ | Δ |
| Comparative Example 3 | Organosilicon Compound #8 | X | X | X |
| Comparative Example 4 | Organosilicon Compound #9 | X | X | X |

As seen from Table 1, the reaction products with alkyl alcohol amines are poor in humidity/temperature stability whereas the sulfur-containing organosilicon compounds within the scope of the invention are improved in humidity/temperature stability and resistant to long-term storage.

Examples 15 to 21 and Comparative Examples 5 to 9

A master batch was prepared by compounding 110 parts of oil-extended emulsion polymerized SBR (#1712 by JSR Corp.), 20 parts of NR (general RSS #3 grade), 20 parts of carbon black (general N234 grade), 50 parts of silica (Nipsil AQ by Nippon Silica Industry Co., Ltd.), 6.5 parts of one of Organosilicon Compounds #1 to #7 or Comparative Compounds A to C, shown below, 1 part of stearic acid, and 1 part of antioxidant (Nocrac 6C by Ouchi Shinko Chemical Industrial Co., Ltd.). To the master batch, 3 parts of zinc white, 0.5 part of vulcanization accelerator DM (dibenzothiazyl disulfide), 1 part of vulcanization accelerator NS (N-t-butyl-2-benzothiazolyl sulfenamide), and 1.5 parts of sulfur were added and kneaded, yielding a rubber composition.

The rubber compositions were measured for physical properties prior to and subsequent to vulcanization. The results are shown in Tables 2 and 3.

[Unvulcanized Physical Properties]
(1) Mooney Viscosity

Mooney viscosity was measured according to JIS K-6300 under conditions including preheat time 1 min., running time 4 min., and temperature 130° C. The viscosity is expressed as an index by normalizing the value of Comparative Example 7 to 100. A lower index value indicates a lower Mooney viscosity and hence, better processing.

[Vulcanized Physical Properties]
(2) Kinematic Viscoelasticity

Using a viscoelasticity meter (Rheometric Scientific, Inc.), measurement was made under conditions, tensile dynamic strain 5%, frequency 15 Hz, and 60° C. The specimen was a sheet of 0.2 cm thick and 0.5 cm wide, with a clamp span of 2 cm and an initial load of 160 g. A tan δ value is expressed as an index by normalizing the value of Comparative Example 7 to 100. A lower index value indicates a lower hysteresis loss and hence, lower heat generation.

(3) Abrasion Resistance

Abrasion resistance was measured according to JIS K-6264-2 (2005), using a Lambourn abrasion tester under conditions, room temperature and slip rate 25%. The abrasion resistance is expressed as an index by normalizing the inverse of abrasion amount of Comparative Example 7 to 100. A higher value indicates a smaller abrasion amount and hence, better abrasion resistance.

Comparative Compound A

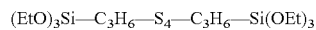

$(EtO)_3Si-C_3H_6-S_4-C_3H_6-Si(OEt)_3$

Comparative Compound B

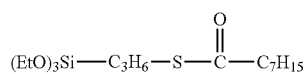

$(EtO)_3Si-C_3H_6-S-\overset{O}{\underset{\|}{C}}-C_7H_{15}$

Comparative Compound C

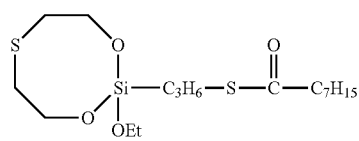

(Et stands for ethyl.)

TABLE 2

| Formulation (pbw) | Example | | | | | | |
|---|---|---|---|---|---|---|---|
| | 15 | 16 | 17 | 18 | 19 | 20 | 21 |
| SBR | 110 | 110 | 110 | 110 | 110 | 110 | 110 |
| NR | 20 | 20 | 20 | 20 | 20 | 20 | 20 |
| Carbon black | 20 | 20 | 20 | 20 | 20 | 20 | 20 |
| Silica | 50 | 50 | 50 | 50 | 50 | 50 | 50 |

TABLE 2-continued

| Formulation (pbw) | Example | | | | | | |
|---|---|---|---|---|---|---|---|
| | 15 | 16 | 17 | 18 | 19 | 20 | 21 |
| Stearic acid | 1 | 1 | 1 | 1 | 1 | 1 | 1 |
| Antioxidant | 1 | 1 | 1 | 1 | 1 | 1 | 1 |
| Zinc white | 3 | 3 | 3 | 3 | 3 | 3 | 3 |
| DM | 0.5 | 0.5 | 0.5 | 0.5 | 0.5 | 0.5 | 0.5 |
| NS | 1 | 1 | 1 | 1 | 1 | 1 | 1 |
| Sulfur | 1.5 | 1.5 | 1.5 | 1.5 | 1.5 | 1.5 | 1.5 |
| Organosilicon Compound #1 | 6.5 | — | — | — | — | — | — |
| Organosilicon Compound #2 | — | 6.5 | — | — | — | — | — |
| Organosilicon Compound #3 | — | — | 6.5 | — | — | — | — |
| Organosilicon Compound #4 | — | — | — | 6.5 | — | — | — |
| Organosilicon Compound #5 | — | — | — | — | 6.5 | — | — |
| Organosilicon Compound #6 | — | — | — | — | — | 6.5 | — |
| Organosilicon Compound #7 | — | — | — | — | — | — | 6.5 |
| Unvulcanized physical properties | | | | | | | |
| Mooney viscosity | 104 | 102 | 104 | 102 | 104 | 103 | 103 |
| Vulcanized physical properties | | | | | | | |
| Kinematic viscoelasticity, tanδ @60° C. | 95 | 95 | 94 | 94 | 94 | 93 | 93 |
| Abrasion resistance | 102 | 102 | 103 | 103 | 104 | 104 | 103 |

TABLE 3

| Formulation (pbw) | Comparative Example | | | | |
|---|---|---|---|---|---|
| | 5 | 6 | 7 | 8 | 9 |
| SBR | 110 | 110 | 110 | 110 | 110 |
| NR | 20 | 20 | 20 | 20 | 20 |
| Carbon black | 20 | 20 | 20 | 20 | 20 |
| Silica | 50 | 50 | 50 | 50 | 50 |
| Stearic acid | 1 | 1 | 1 | 1 | 1 |
| Antioxidant | 1 | 1 | 1 | 1 | 1 |
| Zinc white | 3 | 3 | 3 | 3 | 3 |
| DM | 0.5 | 0.5 | 0.5 | 0.5 | 0.5 |
| NS | 1 | 1 | 1 | 1 | 1 |
| Sulfur | 1.5 | 1.5 | 1.5 | 1.5 | 1.5 |
| Organosilicon Compound #8 | 6.5 | — | — | — | — |
| Organosilicon Compound #9 | — | 6.5 | — | — | — |
| Comparative Compound A | — | — | 6.5 | — | — |
| Comparative Compound B | — | — | — | 6.5 | — |
| Comparative Compound C | — | — | — | — | 6.5 |
| Unvulcanized physical properties | | | | | |
| Mooney viscosity | 108 | 109 | 100 | 98 | 97 |
| Vulcanized physical properties | | | | | |
| Kinematic viscoelasticity, tanδ @60° C. | 94 | 95 | 100 | 99 | 98 |
| Abrasion resistance | 102 | 102 | 100 | 101 | 101 |

As seen from Tables 2 and 3, the sulfur-containing organosilicon compounds within the scope of the invention are effective for significantly reducing the hysteresis loss and improving the abrasion resistance of rubber compositions.

Japanese Patent Application No. 2013-257663 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfur-containing organosilicon compound obtained from transesterification reaction of a sulfide-containing organosilicon compound with an amide compound, said sulfide-containing organosilicon compound having the formula (1):

$$(R^1O)_{(3-p)}(R^2)_p Si-R^3-S_n-R^3-Si(OR^1)_{(3-p)}(R^2)_p \quad (1)$$

wherein $R^1$ and $R^2$ are each independently a monovalent hydrocarbon group of 1 to 4 carbon atoms, $R^3$ is a divalent hydrocarbon group of 1 to 10 carbon atoms, n is a number having an average value in the range of $2 \le n \le 6$, and p is an integer of 0 to 2, said amide compound having the formula (2):

(2)

wherein $R^4$ is a monovalent hydrocarbon group of 1 to 20 carbon atoms, $R^5$ is a group of the formula (3), and $R^6$ is hydrogen, an alkyl group of 1 to 12 carbon atoms, an aryl group of 6 to 12 carbon atoms or a group of the formula (3):

$$*-(CH_2)_s-R^7-OH \quad (3)$$

wherein $R^7$ is an alkylene group of 1 to 12 carbon atoms or $*-O-(Y-O)_m-Y-*$, Y is an alkylene group of 1 to 10 carbon atoms, m is a number of 1 to 40, and s is a number of 0 to 12, and * designates a bonding site.

2. The sulfur-containing organosilicon compound of claim 1 wherein the amide compound having the formula (2) is selected from compounds having the formulae (4) to (7):

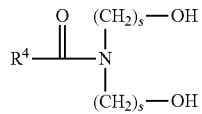
(4)

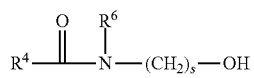
(5)

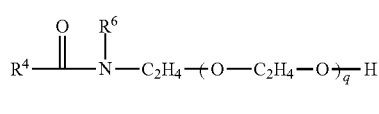
(6)

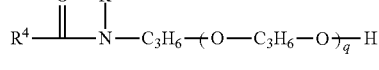
(7)

wherein $R^4$, $R^6$ and s are as defined above, and q is a number of 1 to 40.

3. The sulfur-containing organosilicon compound of claim 1 wherein in the reaction, 1 to 200 parts by weight of the amide compound having formula (2) is used per 100 parts by weight of the sulfide-containing organosilicon compound having formula (1).

4. A method for preparing a sulfur-containing organosilicon compound of claim 1 comprising transesterification reaction of a sulfide-containing organosilicon compound with an amide compound in the presence of a catalyst, said sulfide-containing organosilicon compound having the formula (1):

$$(R^1O)_{(3-p)}(R^2)_p Si-R^3-S_n-R^3-Si(OR^1)_{(3-p)}(R^2)_p \quad (1)$$

wherein $R^1$ and $R^2$ are each independently a monovalent hydrocarbon group of 1 to 4 carbon atoms, $R^3$ is a divalent hydrocarbon group of 1 to 10 carbon atoms, n is a number having an average value in the range of $2 \le n \le 6$, and p is an integer of 0 to 2, said amide compound having the formula (2):

(2)

wherein $R^4$ is a monovalent hydrocarbon group of 1 to 20 carbon atoms, $R^5$ is a group of the formula (3), and $R^6$ is hydrogen, an alkyl group of 1 to 12 carbon atoms, an aryl group of 6 to 12 carbon atoms or a group of the formula (3):

$$*-(CH_2)_s-R^7-OH \quad (3)$$

wherein $R^7$ is an alkylene group of 1 to 12 carbon atoms or $*-O-(Y-O)_m-Y-*$, Y is an alkylene group of 1 to 10 carbon atoms, m is a number of 1 to 40, and s is a number of 0 to 12, and * designates a bonding site.

5. The method of claim 4 wherein the amide compound having the formula (2) is selected from compounds having the formulae (4) to (7):

(4)

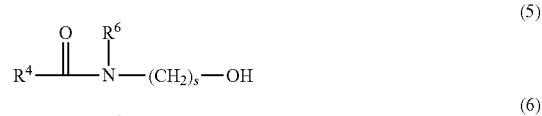
(5)

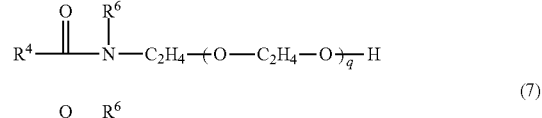
(6)

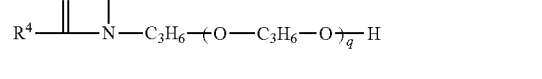
(7)

wherein $R^4$, $R^6$ and s are as defined above, and q is a number of 1 to 40.

6. The method of claim 4 wherein 1 to 200 parts by weight of the amide compound having formula (2) is used per 100 parts by weight of the sulfide-containing organosilicon compound having formula (1).

7. The method of claim 4 wherein the catalyst is an acid, alkaline metal alcoholate, or organometallic catalyst.

8. A rubber compounding ingredient comprising the sulfur-containing organosilicon compound of claim 1.

9. The rubber compounding ingredient of claim 8, further comprising at least one powder, wherein the sulfur-containing organosilicon compound (A) and the at least one powder (B) are present in a weight ratio A/B of 70/30 to 5/95.

10. A rubber composition comprising the rubber compounding ingredient of claim 8.

11. A tire comprising the rubber composition of claim 10.

* * * * *